United States Patent [19]
Hubele et al.

[11] 4,244,962
[45] Jan. 13, 1981

[54] FUNGICIDAL N-(PIPERIDINOACETYL)ANILINES

[75] Inventors: Adolf Hubele, Magden; Walter Kunz, Oberwil, both of Switzerland; Wolfgang Eckhardt, Lörrach, Fed. Rep. of Germany

[73] Assignee: Ciba-Geigy Corporation, Ardsley, N.Y.

[21] Appl. No.: 39,012

[22] Filed: May 14, 1979

Related U.S. Application Data

[62] Division of Ser. No. 905,312, May 12, 1978, Pat. No. 4,165,381, which is a division of Ser. No. 726,320, Sep. 24, 1976, Pat. No. 4,098,895.

[30] Foreign Application Priority Data

Sep. 30, 1975 [CH] Switzerland ............... 12650/75
Sep. 30, 1975 [CH] Switzerland ............... 12651/75

[51] Int. Cl.$^3$ ............... A01N 43/40; C07D 295/14
[52] U.S. Cl. ............... 424/267; 546/233
[58] Field of Search ............... 546/233; 424/267

[56] References Cited

U.S. PATENT DOCUMENTS 3,124,586  3/1964  Zenitz ............... 546/233 X

Primary Examiner—Henry R. Jiles
Assistant Examiner—Richard A. Schwartz
Attorney, Agent, or Firm—Frederick H. Rabin

[57] ABSTRACT

Amino aceto anilides of the formula I shown hereinafter are effective microbicides. They may be used to control fungi on plants or parts of plants or to prevent them from fungi attack.

6 Claims, No Drawings

FUNGICIDAL N-(PIPERIDINOACETYL)ANILINES

This is a division of application Ser. No. 905,312 filed May 12, 1978 now U.S. Pat. No. 4,165,381, which in turn is a division of application Ser. No. 726,370, filed Sept. 24, 1976, now U.S. Pat. No. 4,098,895.

The present invention provides compounds of the formula I

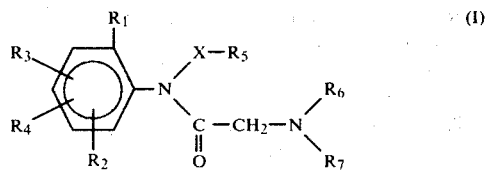

wherein
$R_1$ represents a $C_1$–$C_4$-alkyl group, a $C_1$–$C_4$-alkoxy group or a halogen atom,
$R_2$ represents a hydrogen atom, a $C_1$–$C_3$-alkyl group, a $C_1$–$C_4$-alkoxy group or a halogen atom,
$R_3$ represents a hydrogen atom, a $C_1$–$C_3$-alkyl group or a halogen atom,
$R_4$ represents a hydrogen atom or a methyl group, with the proviso that the total number of carbon atoms contained by the substituents $R_1$, $R_2$, $R_3$ and $R_4$ in the phenyl ring does not exceed 8, and
X represents —$CH_2$— or

$R_5$ represents —COOR′, COSR′ or

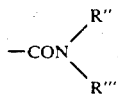

wherein each of R′, R″ and R‴ independently represents a methyl or ethyl group.
$R_6$ represents a hydrogen atom or has a meaning assigned to $R_7$, albeit an independent one,
$R_7$ represents a $C_1$–$C_6$-alkyl group which is unsubstituted or substituted by cyano, hydroxyl or $C_1$–$C_3$-alkoxy, or a $C_3$–$C_6$-alkenyl group which is unsubstituted or substituted by halogen, or else represents a $C_3$–$C_6$-alkynyl or $C_3$–$C_7$-cycloalkyl group, whilst
$R_6$ and $R_7$ together with the nitrogen atom to which they are attached can represent a $C_2$–$C_6$-alkylene or alkenylene group which is unsubstituted or mono- or polysubstituted by halogen or $C_1$–$C_3$-alkyl and which can obtain one or two heteroatoms,
and salts of the compounds of the formula I with inorganic or organic acids.

By alkyl or alkyl moiety of an alkoxy group are meant the following groups, depending on the stated number of carbon atoms: methyl, ethyl, propyl, iso-propyl, butyl, iso-butyl, sec. butyl, tert. butyl, and pentyl and hexyl together with their isomers. By analogy, this definition also applies to the alkylene groups, which together with the nitrogen atom to which they are attached form cyclic amines. An alkylene group containing 2 carbon atoms is accordingly an ethylene group and together with the nitrogen atom to which it is attached forms an aziridine ring. Alkylene groups containing 2 to 6 carbon atoms form corresponding cyclic amines with one or more double bonds, depending on the size of the ring and of the number of heteroatoms which can further be contained in the ring.

Alkenyl is to be understood as meaning for example the following groups: vinyl, propenyl, butenyl, 4-pentenyl. An alkynyl group is chiefly a propargyl group.

Suitable $C_3$–$C_7$-cycloalkyl groups are: cyclopropyl, cyclobutyl, cyclopentyl, cyclohexyl, cycloheptyl groups.

Within the scope of the present invention, heteroatoms are to be understood as meaning oxygen, sulphur and nitrogen atoms. By halogen atoms, which can also be present as substituents of a heterocyclic ring formed by $R_6$ and $R_7$, are meant fluorine, chlorine, bromine or iodine atoms.

Examples of inorganic acids are: hydrochloric acid, hydrobromic acid, hydroiodic acid, sulphuric acid, phosphoric acid, phosphorous acid, perchloric acid, nitric acid, methoxysulphuric acid etc.

Examples of organic acids are: acetic acid, trichloroacetic acid, oxalic acid, succinic acid, maleic acid, lactic acid, glycollic acid, aconitic acid, citric acid, benzoic acid, benzenesulphonic acid, methanesulphonic acid.

The foregoing enumerations cited by way of example are not to be interpreted as implying any limitation thereto. The invention also provides microbicidal compositions which contain a compound of the formula I as active component, and, in addition, a method of combating fungi and bacteria, which comprises the use of the compounds of the formula I.

ω-Aminoacylanilines containing halogen atoms, alkyl or alkoxy groups in the ortho-positions of the phenyl ring are already known. Pyrrocain (=1-pyrrolidine-aceto-2′, 6′-dimethylanilide), which is used as a local anaesthetic, is known from U.S. Pat. No. 2,813,861.

Xylocain (=2-diethylaminoaceto-2′, 6′-dimethylanilide) is also a commercially available local anaesthetic. [Merck Index, 8th Edition, p. 618, (Merck & Co. Inc.]. In South African patent 74/3766, 2-n-butyl-2-tert.butylamino-aceto-2′,6′-dimethylanilide is also proposed as an improved preparation for the same purpose.

Primary amino-acyl-2′, 6′-disubstituted anilides are disclosed in DOS No. 2,400,540 as therapeutic compounds with antiarrhythmic properties. No indication of a microbicidal action on phytopathogenic fungi are given.

The closest comparable substances of this publication, which are referred to as being preferred, such as N-aminoacetyl-2,6-diethylaniline, N-aminoacetyl-2′,6′-diethoxyaniline or N-propyl-N-aminoacetyl-2′,6′-dimethylaniline, are ineffective against pathogens of plant diseases.

The present invention is based on the surprising observation that compounds having the structure of formula I possess for practical purposes a very advantageous microbicidal spectrum for protecting cultivated plants. Examples of cultivated plants within the scope of this invention are: cereals, maize, rice, vegetables, sugar-beet, soya, ground nuts, fruit trees, ornamentals, but primarily vines, hops, cucumber plants (cucumber, marrows, melons), solanaceae, such as potatoes, tobacco plants and tomatoes, and also banana, cocoa and natural rubber plants.

With the active ingredients of the formula I it is possible to inhibit or destroy the fungi which occur in plants or parts of plants (fruit, blossoms, leaves, stems, tubers, roots) in these and also related crops of useful plants, and also to protect from such fungi the parts of plants which grow later. The active ingredients are effective against the phytopathogenic fungi which belong to the following classes: Ascomycetes (e.g. Erysiphaceae); Basidiomycetes, chiefly rust fungi; fungi imperfecti (e.g. Moniliales); but especially against the Oomycetes belonging to the class of the Phycomycetes, such as Phytophthora, Peronospora, Pseudoperonospora, Pythium or Plasmopara. In addition, the compounds of the formula I possess a systemic action. They can also be used as seed dressing agents for protecting seeds (fruit, tubers, grains) and plant cuttings from fungus infections and from phytopathogenic fungi which occur in the soil.

One of the preferred subgroups of compounds of the formula I comprises those compounds wherein $R_1$ represents a methyl group, $R_2$ is in ortho-position to the amino group and represents a methyl or ethyl group or a chlorine atom, —X—$R_5$ possesses the group

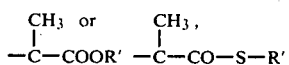

whilst $R_3$, $R_4$, $R_6$, $R_7$ and $R'$ are as previously defined. These compounds shall be referred to as group Ia.

On account of their action, those compounds belonging to group Ia are to be singled out for special mention in which $R_3$ represents a hydrogen atom, a methyl group, a chlorine or bromine atom, $R_4$ represents a hydrogen atom or a methyl group, and $R'$ represents a methyl group, whilst each of $R_6$ and $R_7$ independently represents a $C_1$-$C_3$-alkyl group which is unsubstituted or substituted by $C_1$-$C_3$-alkoxy, or an allyl or chlorallyl group. This subgroup of compounds shall be referred to as group Ib.

A further interesting group of compounds comprises those compounds of the formula I in which $R_1$ represents a methyl or ethyl group, $R_2$ is in ortho-position to the amino group and represents a methyl or ethyl group or a chlorine atom, $R_3$ and $R_4$ represent a hydrogen atom or a methyl group, $R_5$ represents one of the groups —COOR' or —CON(R")(R''') and each of $R_6$ and $R_7$ independently represents a $C_1$-$C_4$-alkyl group or a methoxyethyl group, whilst X, R', R" and R''' are as defined in formula I. These compounds shall be referred to as group Ic.

A group of compounds which are very effective against phytopathogenic fungi comprises those compounds of the formula I'

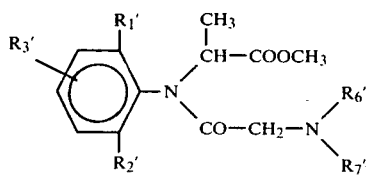

wherein
$R_1'$ represents a methyl or methoxy group,
$R_2'$ represents a methyl or ethyl group or a chlorine atom,
$R_3'$ represents a hydrogen atom, a methyl group, a chlorine or bromine atom,
$R_6'$ represents a methyl, ethyl or n-propyl group, and
$R_7'$ represents a methyl, ethyl, n-propyl or isopropyl group.

From the class of the heterocyclic acylanilides, namely those wherein $R_6$ and $R_7$ together with the nitrogen atom to which they are attached form a ring, those compounds of the formula I are to be singled out for particular mention wherein
$R_1$ represents a methyl or methoxy group,
$R_2$ is in ortho-position to the amino group and represents a methyl or ethyl group, a chlorine or bromine atom,
$R_3$ represents a hydrogen atom, a methyl group, a chlorine or bromine atom,
$R_4$ represents a hydrogen atom or a methyl group, and —X—$R_5$ represents the group —CH(CH$_3$)—COOCH$_3$ or —CH(CH$_3$)—COSCH$_3$, whilst the group —N($R_6$)($R_7$) represents a 5- or 6-numbered heterocyclic ring which is unsubstituted or mono- or di-substituted by halogen or $C_1$-$C_3$-alkyl and which optionally contains one or two further heteroatoms or no heteroatoms. These compounds shall be referred to as group Id.

Within the heterocyclic acylanilides of the group Id, mention is to be made of the ring systems formed from the group —N($R_6$)($R_7$), which can be partially or completely hydrogenated, or conversely, depending on the structural possibility, can contain one or more double bonds: piperidine, monomethylpiperidine, dimethylpiperidine, chloropiperidine, dibromopiperidine, pyrimidine, N-methylpyrimidine, pyridazine, morpholine, thiomorpholine, pyrrole, pyrazole, thiazole, thiazolidine, oxazolidine, triazole. Those compounds belonging to group Id, in which —N($R_6$)($R_7$) forms a pyrazole or 1,2,4-triazole ring, possess a very pronounced microbicidal action. The compounds of group Id which are derived from 1,2,4-triazole are preferred.

Even when used in high concentrations, compounds of the formula I are in general well tolerated by cultivated plants.

According to a further object of the present invention, the compounds of the formula I are obtained (A) by acylating a compound of the formula II

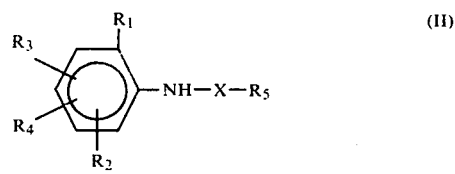

with a carboxylic acid of the formula III

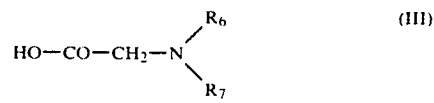

or with the ester or acid anhydride thereof or with the hydrohalide of its acid halide, or (B) by initially correspondingly monohaloacylating a compound of the formula II to give an intermediate of the formula IV

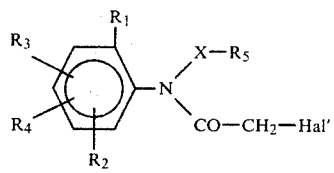

(IV)

and optionally further reacting it with a secondary amine of the formula V

(V)

In the formulae II, III, IV and V, the symbols $R_1$ to $R_7$ and X are as defined in formula I, whilst Hal' represents a halogen atom, preferably a chlorine or bromine atom.

The reactions can be carried out in the presence or absence of solvents or diluents which are inert to the reactants. Examples of suitable solvents or diluents are: aliphatic or aromatic hydrocarbons, such as benzene, toluene, xylenes, petroleum ether; halogenated hydrocarbons, such as chlorobenzene, methylene chloride, ethylene chloride, chloroform; ethers and ethereal compounds, such as dialkyl ethers, dioxane, tetrahydrofurane; nitriles, such as acetonitrile; N,N-dialkylated amides, such as dimethyl formamide; dimethyl sulphoxide; ketones, such as methyl ethyl ketone, and mixtures of such solvents.

The reaction temperatures are between 0° and 180° C., preferably between 20° C. and 120° C. It is often advantageous to use acid acceptors or condensation agents. Suitable examples are: tertiary amines, for example trialkylamines (e.g. triethylamine), pyridine and pyridine bases, or inorganic bases, for example the oxides and hydroxides, hydrogen carbonates and carbonates of alkali metals and alkaline earth metals, and sodium acetate. Moreover, in the first process (A) and in the monohaloacetylation of process (B), it is possible to use an excess of the respective aniline derivative of the formula II as acid acceptor. An excess of a compound of the formula V can also be used as acid acceptor in the further reaction of a compound of the formula IV to give the compound of the formula I.

Process (A), in which compounds of the formula II are used as starting materials, can also be carried out without acid acceptors. On some occasions it is expedient to introduce nitrogen in order to expel the hydrogen halide that has formed, and on others it is very advantageous to use dimethyl formamide as reaction catalyst.

Particulars on the manufacture of the intermediates of the formula II can be inferred from those methods which are generally indicated for the manufacture of anilinoalkanoic acid esters in the following publication:

J. Org. Chem. 30, 4101 (1965); Tetrahedron 1967, 487; Tetrahedron 1967, 493.

The compounds of the formula I, in which X=

contain an asymmetrical carbon atom (*) and can be resolved into the optical antipodes in the customary manner. In this connection, the enantiomeric D-form has the more pronounced microbicidal action.

Within the scope of the invention, those compounds, the compositions which contain them and their use, which refer to the D-configurations of the formula I, are accordingly preferred.

The pure optical D-antipodes are obtained by manufacturing for example the racemic compound of the formula VI

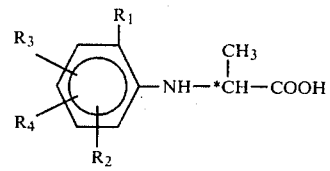

(VI)

wherein $R_1$, $R_2$, $R_3$ and $R_4$ are as defined in formula I, and then reacting it in known manner with a nitrogen-containing optically active base to give the corresponding salt. The pure D-form is obtained stepwise by fractional crystallisation of the salt and subsequent liberation of the acid of the formula VI which is enriched with the optical D-antipode and, if appropriate, repetition (also several times) of the salt formation, crystallisation and liberation of the α-anilino-propionic acid of the formula VI. From this pure D-form it is then possible, if desired, to obtain the optical D-configuration of the ester of the formula II in known manner, for example in the presence of HCl or $H_2SO_4$, with methanol or ethanol or with methyl mercaptan or ethyl mercaptan (or with the alkali salts thereof), or else to obtain the amide of the formula II with the corresponding amine of the formula HN(R")(R'''), preferably by way of the acid halide. A suitable optically active organic base is for example α-phenylethylamine.

Instead of fractional crystallisation, it is also possible to obtain the enantiomeric D-form of the formula VII by diazotising the amino group in the naturally

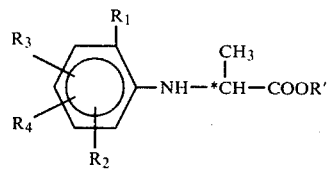

(VII)

occurring L-alanine in the presence, for example, of HCl or HBr, and thereby replacing it by halogen accompanied by the splitting off of $N_2$ and with retention of the L-configuration, then, if appropriate, effecting esterification with methanol or ethanol, and subsequently reacting the ester with the aniline of the formula VIII

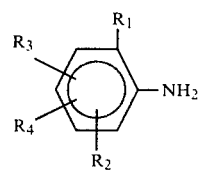

(VIII)

when predominantly inversion to the D-configurations of the formula VII occurs (J. Am. Chem. Soc. 76, 6065). Accordingly, the thiols (in which $R_5$=—COSR') and the amides in which $R_5 = -CON(R'')(R''')$ can also be obtained in this manner.

Irrespective of the cited optical isomerism, an atropisomerism is observed about the phenyl—N< axis in those instances in which the phenyl ring is substituted at least in 2,6-position and at the same time unsymmetrically to this axis (i.e. optionally also on account of the presence of additional substituents).

Provided no synthesis with the object of isolating pure isomers is carried out, a product of the formula I will normally occur as a mixture of these possible isomers. However, the basically more advantageous fungicidal action of the enantiomeric D-form derived from the formula VI (in comparison with the D,L-form or with the L-form) is retained and is not noticeably affected by the atropisomerism.

The following Examples will serve to illustrate the invention in more detail but do not limit it to what is described therein. Unless stated to the contrary, an active substance of the formula I which can occur in optically active forms is always to be understood as meaning the racemic mixture.

EXAMPLE 1

Manufacture of

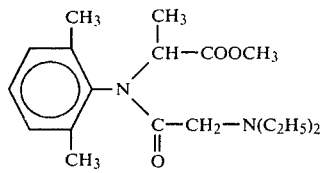
(Compound 1.3)

N-(1'-Methoxycarbonyl-ethyl)-N-diethylaminoacetyl-2,6-dimethylaniline.

(a) Preparation of N-(1'-methoxycarbonyl-ethyl)-N-chloroacetyl-2,6-dimethylaniline (intermediate). 990.3 g (4.76 g-moles) of methyl α-(2,6-dimethylanilino)-propionate are mixed with 605 g (5.7 g-moles) of sodium carbonate in 2.5 litres of absolute benzene. To this mixture are added 455 ml (5.7 g-moles) of monochloroacetyl chloride so slowly that the temperature of the reaction mixture does not exceed 30°–35° C. After the mixture has been stirred overnight at room temperature, it is filtered and the filtrate is concentrated by rotary evaporation at approx. 50° C. The residue is recrystallised from benzine (boiling range 65°–90° C.) to yield 1132 g of intermediate with a melting point of 92°–94° C.

(b) 29 g of the product obtained in (a) and 60 g of diethylamine in 100 ml of water are heated for 60 hours to 80° C. The reaction mixture is then diluted with 200 ml of water, cooled, and extracted with three 200 ml portions of ethyl acetate. The combined extracts are washed with a small amount of water, dried over sodium sulphate and filtered. The ethyl acetate is then evaporated. The crude product is purified by distillation in a high vacuum, b.p. 138°–140° C./0.05 Torr. The oil can be crystallised by trituration with petroleum ether. The colourless crystals of compound 1.3 melt at 28°–32° C. The following compounds of the formula Ie can be obtained in this manner or by one of the methods indicated above:

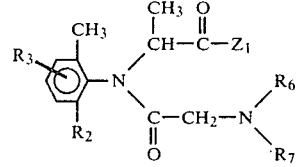

$R_2$ = 6-position

| Compound | $R_2$ | $R_3$ | $Z_1$ | $-N\langle {}^{R_6}_{R_7}$ | Physical constant (temperatures in °C.) |
|---|---|---|---|---|---|
| 1.1 | $CH_3$ | H | $-OCH_3$ | $-N(CH_3)_2$ | m.p. 61–63.5° |
| 1.2 | $CH_3$ | H | $-SCH_3$ | $-N(CH_3)_2$ | m.p. 84–88° |
| 1.3 | $CH_3$ | H | $-OCH_3$ | $-N(C_2H_5)_2$ | m.p. 28–32° |
| 1.4 | $C_2H_5$ | H | $-N(CH_3)_2$ | $-N(CH_3)_2$ | |
| 1.5 | $CH_3$ | H | $-OCH_3$ | $-N(n-C_3H_7)_2$ | b.p. 125°/0.04 Torr. |
| 1.6 | $CH_3$ | H | $-SCH_3$ | $-N(n-C_3H_7)_2$ | b.p. 154°/0.1 Torr. |
| 1.7 | $C_2H_5$ | H | $-N(CH_3)_2$ | $-N(n-C_3H_7)_2$ | |
| 1.8 | $CH_3$ | H | $-OCH_3$ | $-N(n-C_4H_9)_2$ | b.p. 190°/0.2 Torr. |
| 1.9 | $C_2H_5$ | H | $-OCH_3$ | $-N(CH_3)_2$ | |
| 1.10 | $CH_3$ | H | $-OCH_3$ | $-N(n-C_6H_{13})_2$ | b.p. 180°/0.05 Torr. |
| 1.11 | $CH_3$ | H | $-SCH_3$ | $-N(C_2H_5)_2$ | |
| 1.12 | $CH_3$ | H | $-OCH_3$ | $-N(CH_2CH_2OCH_3)_2$ | b.p. 160–165°/0.07 Torr. |
| 1.13 | $CH_3$ | H | $-OCH_3$ | $-N(CH_2-CH=CH_3)_2$ | b.p. 134°/0.05 Torr. |
| 1.14 | $C_2H_5$ | H | $-OCH_3$ | $-N(n-C_3H_7)_2$ | |
| 1.15 | $C_2H_5$ | H | $-OCH_3$ | $-N(C_2H_5)_2$ | b.p. 145°/0.05 Torr. |
| 1.16 | $CH_3$ | H | $-OCH_3$ | $-N(CH_2CH_2OH)_2$ | |
| 1.17 | $C_2H_5$ | H | $-OCH_3$ | $-N\langle {}^{CH_3}_{CH_2CH_2OH}$ | m.p. 84–87° |

-continued

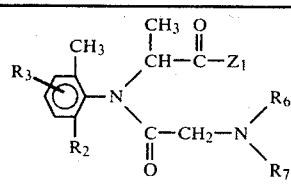
(Ie)

R₂ = 6-position

| Compound | R₂ | R₃ | Z₁ | −N(R₆)(R₇) | Physical constant (temperatures in °C.) |
|---|---|---|---|---|---|
| 1.18 | CH₃ | H | −OCH₃ | −N(CH₃)(CH₂CH₂OH) | m.p. 92–94° |
| 1.19 | C₂H₅ | H | −OCH₃ | −N(CH₂−CH=CH₂)₂ | |
| 1.20 | CH₃ | H | −OCH₃ | −N(CH₂−C(Cl)=CH₂)₂ | b.p. 185°/0.1 Torr. |
| 1.21 | Cl | H | −OCH₃ | −N(CH₂−CH=CH₂)₂ | |
| 1.22 | CH₃ | H | −SCH₃ | −N(CH₂CH₂OCH₃)₂ | b.p. 175°/0.1 Torr. |
| 1.23 | CH₃ | H | −OCH₃ | −N(CH₃)(CH₂CH₂CN) | b.p. 167°/0.2 Torr. |
| 1.24 | Cl | H | −N(CH₃)₂ | −N(n-C₃H₇)₂ | |
| 1.25 | Cl | H | −OCH₃ | −N(CH₃)₂ | m.p. 85–87° |
| 1.26 | CH₃ | H | −OCH₃ | −NH-tert. C₄H₉ | b.p. 147°/0.6 Torr. |
| 1.27 | C₂H₅ | H | −OCH₃ | −NH-tert. C₄H₉ | b.p. 160°/0.15 Torr. |
| 1.28 | Cl | H | −OCH₃ | −N(C₂H₅)₂ | |
| 1.29 | Cl | H | −OCH₃ | −N(CH₃)(CH₂CH₂OH) | b.p. 180–186°/0.04 Torr. |
| 1.30 | C₂H₅ | H | −SCH₃ | −N(CH₃)₂ | b.p. 161°/0.8 Torr. |
| 1.31 | CH₃ | 3-CH₃ | −N(CH₃)₂ | −N(n-C₃H₇)₂ | |
| 1.32 | CH₃ | 4-CH₃ | −SCH₃ | −N(n-C₃H₇)₂ | b.p. 181°/0.8 Torr. |
| 1.33 | CH₃ | 3-CH₃ | −SCH₃ | −N(CH₃)₂ | m.p. 59–61° |
| 1.34 | CH₃ | 3-CH₃ | −OCH₃ | −N(CH₃)₂ | b.p. 155°/0.1 Torr. |
| 1.35 | CH₃ | 3-Br | −OCH₃ | −N(CH₃)₂ | b.p. 187°/0.02 Torr. |
| 1.36 | CH₃ | 3-CH₃ | −OCH₃ | −N(CH₃)₂ | b.p. 150–155°/0.1 Torr. |
| 1.37 | CH₃ | 3-Br | −OCH₃ | −N(n-C₃H₇)₂ | |
| 1.38 | CH₃ | 3-CH₃ | −OCH₃ | −N(C₂H₅)₂ | b.p. 152°/0.04 Torr. |
| 1.39 | −OCH₃ | H | −OCH₃ | −N(CH₃)₂ | |
| 1.40 | CH₃ | 3-CH₃ | −OCH₃ | −N(n-C₃H₇)₂ | b.p. 172°/0.2 Torr. |
| 1.41 | CH₃ | 4-Br | −OCH₃ | −N(CH₃)₂ | |
| 1.42 | CH₃ | 3-CH₃ | −OCH₃ | −N(CH₂−CH=CH₂)₂ | b.p. 160°/0.08 Torr. |
| 1.43 | CH₃ | 4-Br | −OCH₃ | −N(C₂H₅)₂ | |
| 1.44 | CH₃ | 4-Br | −OCH₃ | −N(n-C₃H₇)₂ | |
| 1.45 | CH₃ | 4-Cl | −OCH₃ | −N(n-C₃H₇)₂ | b.p. 168°/0.09 Torr. |
| 1.46 | CH₃ | 4-Br | −OCH₃ | −N(CH₃)(CH₂CH₂OH) | |
| 1.47 | C₂H₅ | 4-Br | −OCH₃ | −N(CH₃)₂ | |
| 1.48 | CH₃ | 4-Br | −OCH₃ | −N(CH₂CH₂OCH₃)₂ | |
| 1.49 | C₂H₅ | 4-Br | −OCH₃ | −N(nC₃H₇)₂ | |
| 1.50 | CH₃ | 4-CH₃ | −OCH₃ | −N(CH₃)₂ | m.p. 50–51° |
| 1.51 | CH₃ | 4-CH₃ | −OCH₃ | −N(C₂H₅) | b.p. 137°/0.07 Torr. |
| 1.52 | CH₃ | 4-CH₃ | −OCH₃ | −N(CH₂−CH=CH₂)₂ | b.p. 147°/0.04 Torr. |
| 1.53 | CH₃ | 4-CH₃ | −SCH₃ | −N(CH₃)₂ | m.p. 65–67° |
| 1.54 | CH₃ | H | −OCH₃ | −N(CH₃)(CH₂−C≡CH) | oil |

-continued

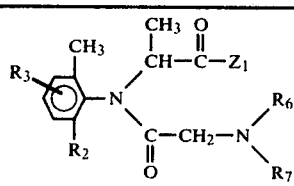
(Ie)

$R_2$ = 6-position

| Compound | $R_2$ | $R_3$ | $Z_1$ | $-N\begin{matrix}R_6\\R_7\end{matrix}$ | Physical constant (temperatures in °C.) |
|---|---|---|---|---|---|
| 1.55 | $CH_3$ | H | $-OCH_3$ | 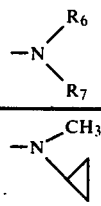 | oil | and the following compounds of the formula 1.56  
C₂H₅ / C₂H₅ phenyl, N-CH(CH₃)-COOCH₃ / CO-CH₂-N(CH₃)₂  — oil 1.57  
O-C₂H₅ / Br phenyl, N-CH(CH₃)-COOCH₃ / CO-CH₂-N(CH₃)₂

1.58  
CH₃, CH₃ / CH₃, CH₃ phenyl, N-CH(CH₃)-COOCH₃ / CO-CH₂-N(C₂H₅)₂

1.59  
CH₃, CH₃ / CH₃, CH₃ phenyl, N-CH(CH₃)-COOCH₃ / CO-CH₂-N(CH₃)₂ — m.p. 118-120°

1.60  
CH₃ / Cl phenyl, N-CH(CH₃)-COOCH₃ / CO-CH₂-N(nC₃H₇)₂

1.61  
CH₃ / CH₃, secC₄H₉O phenyl, N-CH(CH₃)-COOCH₃ / CO-CH₂-N(CH₃)₂ — oil

The following compounds of the formula If can be obtained in this manner or by one of the methods indicated above:

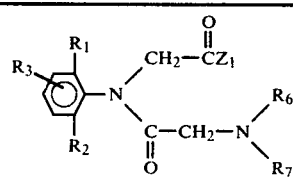
(If)

$R_1$ = 2-position

| Compound | $R_1$ | $R_2$ | $R_3$ | $Z_1$ | $-CH_2-N\begin{matrix}R_6\\R_7\end{matrix}$ | Physical constant (temperatures in °C.) |
|---|---|---|---|---|---|---|
| 1.62 | $C_2H_5$ | $C_2H_5$ | H | $-N(CH_3)_2$ | $-CH_2N(CH_3)_2$ | m.p. 84-87° |
| 1.63 | $CH_3$ | Cl | H | $-N(C_2H_5)_2$ | $-CH_2N(CH_3)_2$ | m.p. 111-113° |
| 1.64 | $CH_3$ | $CH_3$ | H | $-OCH_3$ | $-CH_2N(CH_3)_2$ | |

-continued $$\text{(If)}$$

$R_1$ = 2-position

| Compound | $R_1$ | $R_2$ | $R_3$ | $Z_1$ | $-CH_2-N\begin{matrix}R_6\\R_7\end{matrix}$ | Physical constant (temperatures in °C.) |
|---|---|---|---|---|---|---|
| 1.65 | $CH_3$ | Cl | H | $-N\begin{matrix}C_2H_5\\C_2H_5\end{matrix}$ | $-CH_2N(nCH_3H_7)_2$ | |
| 1.66 | $CH_3$ | $CH_3$ | H | $-OCH_3$ | $-CH_2N(nCH_3H_7)_2$ | |
| 1.67 | $C_2H_5$ | $C_2H_5$ | H | $-N\begin{matrix}C_2H_5\\C_2H_5\end{matrix}$ | $-CH_2N(C_2H_5)_2$ | m.p. 108–115° |
| 1.68 | $CH_3$ | $CH_3$ | 3-$CH_3$ | $-OCH_3$ | $-CH_2-N(C_2H_5)_2$ | |
| 1.69 | $C_2H_5$ | $C_2H_5$ | H | $-N\begin{matrix}CH_3\\CH_3\end{matrix}$ | $-CH_2N(C_2H_5)_2$ | |
| 1.70 | $C_2H_5$ | $C_2H_5$ | H | $-N\begin{matrix}CH_3\\CH_3\end{matrix}$ | $-CH_2N(n\text{-}C_3H_7)_2$ | m.p. 118–126° |
| 1.71 | $C_2H_5$ | $C_2H_5$ | H | $-N\begin{matrix}CH_3\\CH_3\end{matrix}$ | $-CH_2N\begin{matrix}CH_3\\CH_2CH_2OH\end{matrix}$ | |
| 1.72 | $C_2H_5$ | $C_2H_5$ | H | $-N\begin{matrix}CH_3\\CH_3\end{matrix}$ | $-CH_2N(CH_2CH=CH_2)_2$ | |
| 1.73 | $C_2H_5$ | $C_2H_5$ | H | $-N\begin{matrix}CH_3\\CH_3\end{matrix}$ | $-CH_2N(CH_2CH_2OCH_3)_2$ | |
| 1.74 | $C_2H_5$ | $C_2H_5$ | H | $-OCH_3$ | $-CH_2N(C_2H_5)_2$ | m.p. 110–118° |
| 1.75 | $CH_3$ | $CH_3$ | H | $-SC_2H_5$ | $-CH_2N(C_2H_5)_2$ | |

EXAMPLE 2

Manufacture of

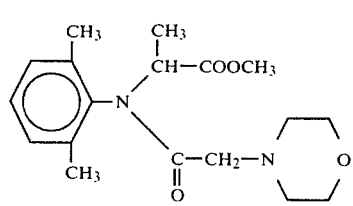

(Compound 2.10)

N-(1′Methoxycarbonyl-ethyl)-N-morpholinoacetyl-2,6-dimethylaniline.

(a) Preparation of N-(1′-Methoxycarbonyl-ethyl)-N-chloroacetyl-2,6-dimethylaniline. 990.3 g (4.76 g-moles) of methyl α-(2,6-dimethylanilino)propionate are mixed with 605 g (5.7 g-moles) of sodium carbonate in 2.5 liters of absolute benzene. To this mixture are added 455 ml (5.7 g-moles) of monochloroacetyl chloride so slowly that the temperature of the reaction mixture does not exceed 30°–35° C. After the mixture has been stirred overnight at room temperature, it is filtered and the filtrate is concentrated by rotary evaporation at approx. 50° C. The residue is recrystallised from benzine (boiling range 65°–90° C.) to yield 1132 g of intermediate with a melting point of 92°–94° C.

(b) 29 g of the product obtained in (a) and 44 g of morpholine in 100 ml of water are heated for 20 hours to 100° C. The reaction mixture is then cooled and extracted with two 150 ml portions of toluene. The combined extracts are washed with a small amount of water, dried over sodium sulphate and filtered. The solvent is then evaporated. The resultant oil can be crystallised by trituration with petroleum ether. After recrystallisation from toluene/petroleum ether, compound 2.10 has a melting point of 77°–79° C.

EXAMPLE 3

Manufacture of

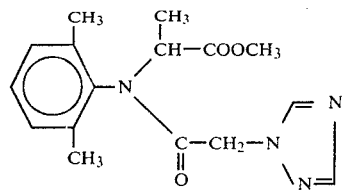

(Compound 2.20)

N-(1'-methoxycarbonyl-ethyl-N-(1,2,4-triazol-1-yl)-acetyl-2,6-dimethylaniline.

In an atmosphere of nitrogen, 20.8 g of 1,2,4-triazole in 100 ml of tetrahydrofurane are added dropwise to 14.4 g of 50% sodium hydride in 60 ml of tetrahydrofurane and the reaction mixture is refluxed for 3 hours until complete formation of the sodium salt has taken place. After cooling to 0° C., 42.5 g of N-(1'-methoxycarbonyl-ethyl)-N-chloroacetyl-2,6-dimethylaniline in 200 ml of tetrahydrofurane are slowly added with stirring. The batch is stirred for 12 hours at room temperature and refluxed for 48 hours. After cooling, 20 ml of water are added in an atmosphere of nitrogen. The mixture is then poured onto ice-water and extracted with three 100 ml portions of diethyl ether. The combined extracts are dried over sodium sulphate and filtered. The diethyl ether is evaporated. After recrystallisation from toluene/petroleum ether, compound 2.20 melts at 131°–132° C. The following compounds of the formula Ig are obtained in this manner or by one of the methods indicated above:

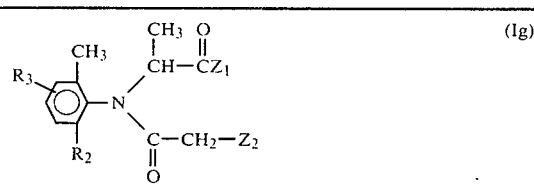

$R_2$ = 6-position

| Compound | $R_2$ | $R_3$ | $Z_1$ | $Z_2$ | Physical Constant (temperatures in °C.) |
|---|---|---|---|---|---|
| 2.1 | $CH_3$ | H | $-OCH_3$ | $-N(CH_2)(CH_2)$ | m.p. 68–72° |
| 2.2 | $-C_2H_5$ | H | $-OCH_3$ | $-N$ (pyrrolidinyl) | b.p. 153°/0.01 Torr. |
| 2.3 | $CH_3$ | H | $-SCH_3$ | $-N(CH_2)(CH_2)$ | viscous |
| 2.4 | $-CH_3$ | H | $-OCH_3$ | $-N$ (pyrrolidinyl) | m.p. 58.5–60° |
| 2.5 | $-C_2H_5$ | H | $-OCH_3$ | $-N\smile O$ (morpholino) | b.p. 167°/0.6 Torr |
| 2.6 | $-CH_3$ | H | $-OCH_3$ | $-N\smile N-CH_3$ | b.p. 180°/0.1 Torr |
| 2.7 | $-CH_3$ | H | $-OCH_3$ | $-N$ (imidazolyl) | oil |
| 2.8 | $-CH_3$ | H | $-OCH_3$ | $-N$ (imidazolyl) · $CH_3COOH$ | >300° (decomp.) |
| 2.9 | $-CH_3$ | 3-$CH_3$ | $-OCH_3$ | $-N$ (imidazolyl) | oil |

-continued

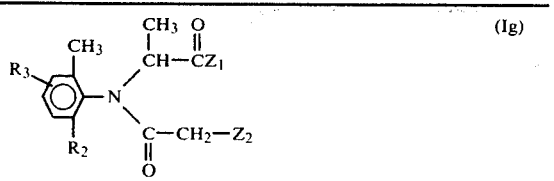

$R_2$ = 6-position

| Compound | $R_2$ | $R_3$ | $Z_1$ | $Z_2$ | Physical Constant (temperatures in °C.) |
|---|---|---|---|---|---|
| 2.10 | —CH₃ | H | —OCH₃ | —N(morpholino) | m.p. 77–79° |
| 2.11 | —C₂H₅ | H | —OCH₃ | —N(piperidino) | b.p. 158–162° C./0.4 Torr |
| 2.12 | —CH₃ | H | —OCH₃ | —N(2,6-dimethylmorpholino) | b.p. 168–170°/0.5 Torr |
| 2.13 | —CH₃ | H | —OCH₃ | —N(2-methylpiperidino) | b.p. 198–°/1.5 Torr |
| 2.14 | —CH₃ | H | —OCH₃ | —N(4-chloropiperidino) | oil |
| 2.15 | —CH₃ | H | —OCH₃ | —N(piperidino) | b.p. 148–154°/0.2 Torr |
| 2.16 | —CH₃ | H | —OCH₃ | —N(2-methyl-2-imidazolin-1-yl) | oil (viscous) |
| 2.17 | —Cl | H | —OCH₃ | —N(piperidino) | b.p. 175–178°/0.9 Torr |
| 2.18 | —CH₃ | H | —OCH₃ | —N(2-methylpiperazin-1-yl) | oil |
| 2.19 | —CH₃ | H | —OCH₃ | —N(pyrrolyl) | b.p. 168–172°/0.05 Torr |

The following compounds of the formula Ih are obtained in this manner or by one of the methods indicated above:

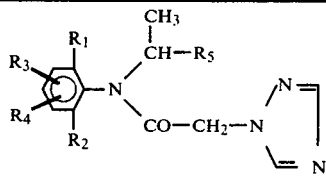

$R_1$ = 2-position

| Compound | $R_1$ | $R_2$ | $R_3$ | $R_4$ | $R_5$ | Physical Constant (temperatures in °C.) |
|---|---|---|---|---|---|---|
| 2.20 | $CH_3$ | $CH_3$ | H | H | $-COOCH_3$ | m.p. 131–132° |
| 2.21 | $CH_3$ | $CH_3$ | H | H | $-CO-SCH_3$ | m.p. 148–151° |
| 2.22 | $CH_3$ | $CH_3$ | 3-$CH_3$ | H | $-COOCH_3$ | resin |
| 2.23 | $CH_3$ | $CH_3$ | 3-$CH_3$ | H | $-CO-SCH_3$ | viscous |
| 2.24 | $CH_3$ | $C_2H_5$ | H | H | $-COOCH_3$ | b.p. 162°/0.01 Torr. |
| 2.25 | $CH_3$ | $C_2H_5$ | H | H | $-CO-SCH_3$ | b.p. 148°/0.08 Torr. |
| 2.26 | $CH_3$ | $CH_3$ | 4-Cl | H | $-COOCH_3$ | m.p. 135–137° |
| 2.27 | $CH_3$ | $C_2H_5$ | 4-Br | H | $-COOCH_3$ | m.p. 119–120° |
| 2.28 | $CH_3$ | $CH_3$ | H | H | $-COOC_2H_5$ | m.p. 137–139° |
| 2.29 | $CH_3$ | H | 5-$CH_3$ | H | $-COOCH_3$ | m.p. 130–132° |
| 2.30 | $CH_3$ | Cl | H | H | $-COOCH_3$ | m.p. 109–112° |
| 2.31 | $CH_3O$ | $CH_3$ | H | H | $-COOOCH_3$ | m.p. 150–152° |
| 2.32 | $CH_3$ | Cl | H | H | $-CO-SCH_3$ | viscous |
| 2.33 | $CH_3$ | $CH_3$ | 3-$CH_3$ | 5-$CH_3$ | $-COOCH_3$ | m.p. 105–108° |
| 2.34 | $CH_3$ | $CH_3$ | 3-$CH_3$ | 5-$CH_3$ | $-CO-SCH_3$ | m.p. 123–125° |
| 2.35 | $CH_3$ | iso$C_3H_7$ | H | H | $-COOCH_3$ | m.p. 95–98° |

The compounds of the formula Ii are also obtained in corresponding manner:

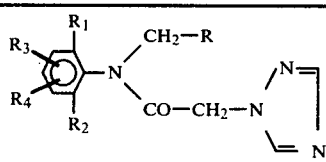

| Compound | $R_1$ | $R_2$ | $R_3$ | $R_4$ | $R_5$ | Physical Constant (temperatures in °C.) |
|---|---|---|---|---|---|---|
| 2.36 | $CH_3$ | $CH_3$ | H | H | $-COOCH_3$ | b.p. 175°/0.01 Torr. |
| 2.37 | $CH_3$ | $CH_3$ | 3-$CH_3$ | H | $-COOCH_3$ | b.p. 147°/0.006 Torr. |
| 2.38 | $CH_3$ | $CH_3$ | 3-$CH_3$ | 5-$CH_3$ | $-COOCH_3$ | b.p. 158°/0.003 Torr. |
| 2.39 | $CH_3$ | $CH_3$ | H | H | $-CO-S-CH_3$ | viscous |

The following compounds of the formula Ij are also obtained in this manner or by one of the methods indicated above:

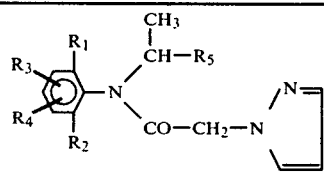

$R_1$ = 2-position

| Compound | $R_1$ | $R_2$ | $R_3$ | $R_4$ | $R_5$ | Physical Constant (temperatures in °C.) |
|---|---|---|---|---|---|---|
| 2.40 | $CH_3$ | $CH_3$ | H | H | $-COOCH_3$ | $n_D^{22}$ 1.5222 |
| 2.41 | $CH_3$ | $CH_3$ | H | H | $-COSCH_3$ | viscous |
| 2.42 | $CH_3$ | $CH_3$ | 3-$CH_3$ | H | $-COOCH_3$ | viscous |
| 2.43 | $CH_3$ | $CH_3$ | 3-$CH_3$ | 5-$CH_3$ | $-COOCH_3$ | b.p. 162°/0.001 Torr. |
| 2.44 | $CH_3$ | $C_2H_5$ | H | H | $-COOCH_3$ | b.p. 108°/0.02 Torr. |
| 2.45 | $C_2H_5$ | $C_2H_5$ | H | H | $-COOCH_3$ | b.p. 132°/0.09 Torr. |
| 2.46 | $CH_3$ | Cl | H | H | $-COOCH_3$ | b.p. 115°/0.02 Torr. |
| 2.47 | $CH_3$ | Br | 4-Cl | H | $-COOCH_3$ | b.p. 153°/0.008 Torr. |
| 2.48 | $CH_3O$ | $CH_3$ | H | H | $-COOCH_3$ | b.p. 124°/0.06 Torr. |
| 2.49 | $CH_3O$ | Cl | H | H | $-COOCH_3$ | b.p. 148°/0.03 Torr. |

The compounds of the formula I can be used by themselves or together with suitable carriers and/or other additives. Suitable carriers and additives can be solid or liquid and correspond to the customary substances used in the art of formulation, for example natural or regenerated mineral substances, solvents, dispersants, wetting agents, tackifiers, thickeners, binders or fertilisers. The preparation of these compositions is effected in known manner by intimately mixing and grinding the constituents.

For application the active substances may take, and be used in, the following forms:

Solid forms:
 dusts, tracking agents, granules, coated granules, impregnated granules and homogeneous granules.

Liquid forms:
 (a) active substance concentrates which are dispersible in water: wettable powders, pastes, emulsions; concentrated solutions.
 (b) Solutions; aerosols.

The content of active substance in the above described compositions is between 0.1% and 95%.

It will be readily understood that the compounds of the formula I can be used together with other suitable pesticides, for example fungicides, insecticides, acaricides or active substances which influence plant growth, in order to adapt them to prevailing circumstances and to broaden their activity spectrum.

For application the active substances of the formula I can be formulated, for example, as follows:

Dusts

The following substances are used to prepare
(a) 5% and
(b) a 2% dust:

(a)
5 parts of active substance
95 parts of talc;

(b)
2 parts of active substance
1 part of highly dispersed silicic acid
97 parts of talc.

The active substances are mixed with the carriers and ground and in this form can be processed to dusts for application.

Granulate

The following substances are used to prepare a 5% granulate:
5 parts of active substances
0.25 parts of epichlorohydrin
0.25 parts of cetyl polyglycol ether
3.50 parts of polyethylene glycol
91 parts of kaolin (particle size 0.3–0.8 mm). The active substance is mixed with epichlorohydrin and the mixture is dissolved in 6 parts of acetone. Then polyethylene glycol and cetyl polyglycol ether are added. The resultant solution is sprayed on kaolin and the acetone is evaporated in vacuo. Such a microgranulate is advantageously used for combating soil fungi.

Wettable powders

The following constituents are used to prepare (a) a 70%, (b) a 40%, (c) and (d) a 25% and (e) a 10% wettable powder:

(a)
70 parts of active substance
5 parts of sodium dibutyl naphthylsulphonate
3 parts of naphthalenesulphonic acid/phenolsulphonic acid/formaldehyde condensate (3:2:1)
10 parts of kaolin
12 parts of Champagne chalk (b)
40 parts of active substance
5 parts of sodium lignin sulphonate
1 part of sodium dibutylnaphthalenesulphonc acid
54 parts of silicic acid (c)
25 parts of active substance
4.5 parts of calcium lignin sulphonate
1.9 parts of Champagne chalk/hydroxyethyl cellulose mixture (1:1)
1.5 parts of sodium dibutylnaphthalenesulphonate
19.5 parts of silicic acid
19.5 parts of Champagne chalk
28.1 parts of kaolin (d)
25 parts of active substance
2.5 parts of isooctylphenoxy-polyethylene-ethanol
1.7 parts of a Champagne chalk/hydroxyethyl cellulose mixture (1:1)
8.3 parts of sodium aluminium silicate
16.5 parts of kieselguhr
46 parts of kaolin (e)
10 parts of active substance
3 parts of a mixture of the sodium salts of saturated fatty alcohol sulphates
5 parts of naphthalenesulphonic acid/formaldehyde condensate
82 parts of kaolin.

The active substances are intimately mixed in suitable mixers with the additives and ground in appropriate mills and rollers. Wettable powders of excellent wettability and suspension powder are obtained. These wettable powders can be diluted with water to give suspensions of the desired concentration and can be used in particular for leaf application.

Emulsifiable concentrates

The following substances are used to prepare a 25% emulsifiable concentrate:
25 parts of active substance
2.5 parts of epoxidised vegetable oil
10 parts of an alkylarylsulphonate/fatty alcohol polyglycol ether mixture
5 parts of dimethyl formamide
57.5 parts of xylene.

By diluting such a concentrate with water it is possible to prepare emulsions of the desired concentration, which are especially suitable for leaf application.

EXAMPLE 4

Action on Phytophthora infestans on tomato plants (Ia) Residual preventive action Tomato plants of the "Roter Gnom" variety are infected when 3 weeks old with a zoospore suspension of Phytophthora infestans after they have been sprayed with a broth (prepared from the active substance formulated as a wettable powder) containing 0.05% of active substance, and dried. The plants are then kept for 6 days in a climatic chamber at 18° to 20° C. and high humidity, which is produced by means of an artificial wet fog. After this time typical leaf specks appear. The effectiveness of the tested substance is assessed by determining the number and size of these specks.

(Ib) Curative Action

"Roter Gnom" tomato plants are sprayed when 3 weeks old with a zoospore suspension of the fungus and incubated in a climatic chamber at 18° to 20° C. and saturated humidity. The humidifying is interrupted after 24 hours. After the plants have dried, they are sprayed with a broth which contains the active substance formulated as a wettable powder in a concentration of 0.05%. After the spray coating has dried, the plants are again kept in the humid chamber for 4 days. The effectiveness of the tested substances is assessed by determining the size and number of the typical leaf specks which have occurred during this time.

(II) Preventive-systemic action

The active substance is applied as a wettable powder in a concentration of 0.05% (referred to the volume of the soil) to the surface of the soil of 3 week old "Roter Gnom" tomatoes in pots. Three days later the underside of the leaves of the plants are sprayed with a zoospore suspension of Phytophthora infestans. The plants are then kept in a spray chamber a 18° to 20° C. and saturated humidity for 5 days, after which time typical leaf specks form. The effectiveness of the tested substance is assessed by determining the size and number of the specks.

In these three tests, the compounds of the formula I effected a pronounced leaf-fungicidal action.

Compounds of groups Ib and Id reduce the fungus attack on average to below 20%. Compounds of the subformula I' and those of the formulae Ih and Ij inhibit the fungus attack completely or almost completely (0-10%). Infected, untreated tomato plants were used as controls (=100% attack).

EXAMPLE 5

Action on Plasmopara viticola (Bert. et Curt.) (Berl. et de Toni) on vines (a) Residual preventive action Vine cuttings of the variety "Chasselas" were reared in a greenhouse. Three plants in the 10 leaf stage were sprayed with a broth (containing 0.05% of active substance) prepared from the active substance and formulated as a wettable powder. After the coating layer had dried, the plants were infected on the underside of the leaves with the spore suspension of the fungus. The plants were subsequently kept in a humid chamber for 8 days, after which time symptoms of the disease were visible on the control plants. The effectiveness of the tested substances was assessed by determining the number and size of the infected areas on the treated plants.

(b) Curative action

Vine cuttings of the variety "Chasselas" were reared in a greenhouse and infected in the 10 leaf stage on the underside of the leaves with a spore suspension of Plasmopara viticola. After they had been kept for 24 hours in a humid chamber, the plants were sprayed with a 0.05% broth prepared from a wettable powder of the active substance. The plants were then kept in a humid chamber for a further 7 days, after which time the symptoms of the disease were visible on the control plants. The effectiveness of the tested substances was assessed by determining the size and number of the infected areas.

In both these tests the compounds of the formula I effected a good leaf-fungicidal action. The fungus attack on the vines was reduced on average to less than 20% in comparison with control plants. Compounds of the subgroups Ib and Id as well as those of subformula I' were particularly effective. Many of the compounds, for example compounds 1.1, 1.2, 1.3, 1.5, 1.6, 1.9, 1.13, 1.15, 1.18, 1.30, 1.34, 1.35, 1.36, 1.38, 1.39, 1.40, 1.54, 1.59, 1.60, and also 2.13, 2.20 to 2.25, 2.30, 2.31, 2.33, 2.34 and 2.40, control the fungus attack completely or almost completely (0-5% attack) even when used in active substance concentrations of 0.02%.

EXAMPLE 6

Action on Pythium debaryanum on sugar beets (Beta vulgaris)

(a) Action after soil application

The fungus is cultivated on sterile oat grains and added to a mixture of earth and sand. Flower pots are filled with the infected soil in which sugar beet seeds are then sown. Immediately after sowing, the test preparations formulated as wettable powders are poured in the form of aqueous suspensions over the soil (20 ppm of active substance referred to the volume of the soil). The pots are then stood for 2-3 weeks in a greenhouse at 20°-24° C. The soil is kept uniformly moist by gently spraying it with water. The emergence of the sugar beet plants as well as the number of healthy and sick plants are ascertained in evaluating the tests.

(b) Action after seed dressing application

The fungus is cultivated on sterile oat grains and added to a mixture of earth and sand. Flower pots are filled with the infected soil and sugar beet seeds which have been treated with the test preparations formulated as seed dressing powders are sown therein (1000 ppm of active substance referred to the weight of the seeds). The pots are then stood in a greenhouse for 2-3 weeks at 20°-24° C. The soil is kept uniformly moist by gently spraying it with water. The emergence of the sugar beet plants as well as the number of healthy and sick plants are ascertained.

Under the conditions of both test (a) and test (b), more than 80% of the sugar beet plants emerged after treatment with the active substances of the formula I and had a healthy appearance.

The pronounced action of compounds 2.21, 2.22 and 2.33, which completely suppress a Pythium attack, is to be singled out for particular mention.

EXAMPLE 7

Action on Cercospora arachidicola on ground nut plants (*Arachis hypogaea*)

Residual protective action

Ground nut plants, 10 to 15 cm in height, were sprayed with a spray broth (containing 0.02% of active substance) prepared from a wettable powder of the active substance, and 48 hours later infected with a conidia suspension of the fungus. The infected plants were incubated for 24 hours at approx. 21° C. and high humidity and subsequently stood in a greenhouse until the occurrence of the typical leaf specks. The evaluation of the fungicidal action, based on the number and size of the specks, was made 12 days after the infection.

In comparison with infected, untreated control plants, the fungus attack was markedly inhibited in plants treated with active compounds of the formula I, in particular when using compounds 1.27, 1.30, 1.53 and 1.56 (attack 0–5%).

We claim:

1. A compound of the formula

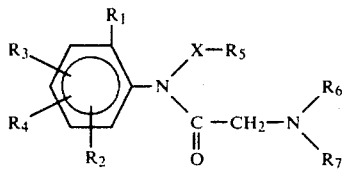

wherein $R_1$ represents a $C_1$–$C_4$-alkyl group, a $C_1$–$C_4$-alkoxy group or a halogen atom, $R^2$ represents a hydrogen atom, a $C_1$–$C_3$-alkyl group, a $C_1$–$C_4$-alkoxy group or a halogen atom, $R_3$ represents a hydrogen atom, a $C_1$–$C_3$-alkyl group or a halogen atom, $R_4$ represents a hydrogen atom or a methyl group, with the proviso that the total number of carbon atoms contained by the substituents $R_1$, $R_2$, $R_3$ and $R_4$ in the phenyl ring does not exceed 8, and X represents —CH$_2$— or

$R_5$ represents —COOR', —COSR' or

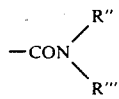

wherein each of R', R" and R''' independently represents a methyl or ethyl group, $R_6$ and $R_7$ together with the nitrogen atom to which they are attached represents piperidino which is unsubstituted or mono- or polysubstituted by halogen or $C_1$–$C_3$-alkyl, or a salt of a compound of the formula I with an inorganic or organic acid.

2. A compound of the formula I according to claim 1, wherein $R_1$ represents a methyl group, $R_2$ is in ortho-position to the amino group and represents a methyl or ethyl group or a chlorine atom, and —X—$R_5$ represents the group —CH(CH$_3$)—COOR' or —CH(CH$_3$)—CO—S—R'.

3. A compound of the formula I according to claim 1, wherein $R_1$ represents a methyl or methoxy group, $R_2$ is in ortho-position to the amino group and represents a methyl or ethyl group, a chlorine or bromine atom, $R_3$ represents a hydrogen atom, a methyl group, a chlorine or bromine atom, $R_4$ represents a hydrogen atom or a methyl group, —X—$R_5$ represents the group —CH(CH$_3$)—COOCH$_3$ or —CH(CH$_3$)—COSCH$_3$, and the group —N($R_6$)($R_7$) represents piperidino which is unsubstituted or mono- or di-substituted by halogen or $C_1$–$C_3$-alkyl.

4. N-(1'-Methoxycarbonyl-ethyl)-N-(2"-methyl-piperidinoacetyl)-2,6-dimethylaniline according to claim 1.

5. A fungicidal composition which contains as active component a fungicidally effective amount of a compound of the formula I according to claim 1, together with a suitable carrier therefor.

6. A method of controlling phytophathogenic fungi or of preventing fungus attack, which comprises applying to plants, parts of plants or their environment, a fungicidally effective amount of a compound of the formula I according to claim 1.

* * * * *